United States Patent
Nallakrishnan (10) Patent No.: US 11,160,652 B2
(45) Date of Patent: Nov. 2, 2021

(54) IOL INJECTOR

(75) Inventor: Ravi Nallakrishnan, Westmont, IL (US)

(73) Assignee: ART, Limited, Grand Cayman (KY)

( * ) Notice: Subject to any disclaimer, the term of this patent is extended or adjusted under 35 U.S.C. 154(b) by 256 days.

(21) Appl. No.: 12/543,399

(22) Filed: Aug. 18, 2009

(65) Prior Publication Data
US 2015/0066043 A1    Mar. 5, 2015

Related U.S. Application Data

(60) Provisional application No. 61/095,860, filed on Sep. 10, 2008.

(51) Int. Cl.
*A61F 2/16*    (2006.01)

(52) U.S. Cl.
CPC ...... *A61F 2/167* (2013.01); *A61F 2250/0073* (2013.01)

(58) Field of Classification Search
CPC .... A61F 2/1664; A61F 2/1662; A61F 2/1667; A61F 2/167; A61F 2/1672; A61F 2/1675; A61F 2/1691; A61F 9/00736; A61F 2/1678; A61F 2/16; A61F 2/1601; A61F 2/16015; A61F 2002/1681; A61F 2002/1682; A61F 2002/1683; A61F 2002/1686; A61F 2002/1689; A61F 2002/169; A61F 2002/16903; A61F 9/0008; A61F 9/0017; A61F 9/0026; A61F 9/00745; A61F 9/00754; A61F 9/00763; A61F 9/007; A61F 9/00709; A51F 2250/0073; A61M 5/31505; A61M 2005/31508; A61M 2005/3151; A61M 2005/31506; A61M 5/315; A61M 5/31501; A61M 5/31511; A61M 5/31513; A61M 5/31515; A61M 5/31536; A61M 5/31576; A61M 5/31578; A61M 5/3158; A61M 5/31581; A61M 5/5013; A61M 5/502; A61M 2005/2086; A61M 2005/5033; A61M 37/0069; A61M 5/3129; A61M 2005/3131
USPC .......................................... 606/107; 623/6.12
See application file for complete search history.

(56) References Cited

U.S. PATENT DOCUMENTS

| | | | | |
|---|---|---|---|---|
| 4,880,000 | A * | 11/1989 | Holmes | A61F 2/1678 606/107 |
| 4,988,339 | A * | 1/1991 | Vadher | A61M 5/3137 604/117 |
| 5,222,947 | A * | 6/1993 | D'Amico | A61M 5/3129 604/198 |
| 5,620,450 | A * | 4/1997 | Eagles | A61F 2/167 606/107 |
| 5,643,276 | A * | 7/1997 | Zaleski | 606/107 |

(Continued)

FOREIGN PATENT DOCUMENTS

| EP | 1941846 A1 * | 7/2008 | ........... A61F 2/1678 |
|---|---|---|---|
| WO | WO 2006059183 A1 * | 6/2006 | |
| WO | WO-2008019430 A1 * | 2/2008 | ........... A61M 5/5013 |

*Primary Examiner* — Katherine H Schwiker
(74) *Attorney, Agent, or Firm* — Wood, Phillips, Katz, Clark & Mortimer (57) ABSTRACT

An injector for intraocular lenses has a housing and a plunger movable within the housing. An elastomeric sleeve is sized and shaped to fit around a portion of the plunger, providing damping friction opposing the movement of the plunger. The sleeve is sterile and disposable, allowing a new sleeve to be used for each procedure.

18 Claims, 4 Drawing Sheets

(56) References Cited

U.S. PATENT DOCUMENTS

| | | | |
|---|---|---|---|
| 5,772,666 A * | 6/1998 | Feingold et al. | 606/107 |
| 5,873,879 A * | 2/1999 | Figueroa | A61F 2/167 |
| | | | 606/107 |
| 6,379,337 B1 * | 4/2002 | Mohammad | A61M 5/322 |
| | | | 604/162 |
| 2002/0058884 A1 * | 5/2002 | Burbank | A61B 10/0266 |
| | | | 600/564 |
| 2004/0059343 A1 * | 3/2004 | Shearer et al. | 606/107 |
| 2005/0149057 A1 * | 7/2005 | Rathert | A61F 2/167 |
| | | | 606/107 |
| 2005/0203542 A1 * | 9/2005 | Weber | A61F 2/167 |
| | | | 606/107 |
| 2005/0240149 A1 * | 10/2005 | Lu | A61M 5/5013 |
| | | | 604/110 |
| 2005/0267416 A1 * | 12/2005 | Mohammed | A61M 5/3232 |
| | | | 604/198 |
| 2006/0085013 A1 * | 4/2006 | Dusek et al. | 606/107 |
| 2006/0089602 A1 * | 4/2006 | Boucherie | A61M 5/31511 |
| | | | 604/218 |
| 2006/0258977 A1 * | 11/2006 | Lee | A61M 5/31596 |
| | | | 604/82 |
| 2009/0005788 A1 * | 1/2009 | Rathert | A61F 2/1662 |
| | | | 606/107 |
| 2010/0204704 A1 * | 8/2010 | Davies | A61F 2/1664 |
| | | | 606/107 |

* cited by examiner

IOL INJECTOR

PRIORITY

This application claims priority from U.S. Patent Application Ser. No. 61/095,860, filed Sep. 10, 2008, which is hereby incorporated herein in its entirety by reference.

FIELD OF THE INVENTION

The present invention relates generally to instruments for eye surgery and, more particularly, to an injector for expressing an intraocular lens (IOL) from a lens injection cartridge.

BACKGROUND OF THE INVENTION

Removing an injured or diseased lens from the eye and replacing it with a foldable, artificial intraocular lens (IOL) is an accepted ophthalmic procedure. The use of hydrogels, silicones and soft acrylics have made replacement IOLs easy to fold, and a number of techniques have been developed to fold the IOL and inject it through an incision smaller than would be required if the IOL were unfolded.

One such technique is to place the IOL into an injector cartridge and use as specially-designed injector tool to push the IOL from the cartridge and express it into the capsular bag. A typical cartridge will have an interior chamber into which the IOL is inserted and a nozzle communicating with the interior chamber. In use, the tip of the nozzle is inserted through an incision made in the eye. Certain cartridges are designed to fold or roll the IOL as it passes through the chamber, while others are designed to open to allow the IOL to be positioned therein, then are closed to fold or roll the IOL and hold the IOL in that position.

Injectors for use with IOL cartridges are well-known and typically comprise a hollow body with a station at one end designed to accept a cartridge that has been preloaded with an IOL. A plunger assembly is slidably received within the injector body and has plunger a handle which extends from the other end of the body. To express the IOL from the cartridge the plunger handle is advanced toward the cartridge until the plunger end contacts the IOL. Continued advance of the plunger end forces the IOL from the cartridge body through the cartridge nozzle and into the eye.

In some injectors the plunger is threadably attached to the injector body and is advanced by turning the plunger, with the rate of advance determined by the pitch of the threads formed on the body and the plunger. Other plungers are slidably received by the injector body and are advanced by pushing the plunger by hand Such injectors may have a guide formed on the interior of the injector body that keeps the plunger moving in a straight line when it is advanced manually. One such type of guide comprises a groove formed on the interior surface of the body and a peg formed on the plunger which fits into and is guided by the groove.

Advancing the plunger manually requires the user to "feel" the changes in resistance to movement that occurs when the IOL is pushed through the cartridge body and nozzle. In some cartridges, a central passageway is formed asymmetrically to roll or fold the IOL as it is pushed through. As the rolling or folding occurs, the resistance to motion changes. Similarly, when the IOL is to be expressed from the cartridge and into the eye, it must pass through a nozzle which is narrowed and which requires a different amount of force to move the IOL.

Prior art injectors have used expedients such as internal or external springs to apply a force opposing the movement of the plunger. This force is intended to damp the movement of the plunger creating a more secure feel to the operation of the injector and giving the user more control over the movement of the plunger.

While the use of springs has added a degree of control, the presence of the springs makes the injector more difficult to assemble and sterilize, and the characteristics of the spring may change over time as the instrument is re-used.

I have determined that adding a damping sleeve to an internal portion of the plunger adds a degree of control. Preferably, the sleeve is disposable meaning that a new sleeve is used each time the injector is used so that the issue of wear is obviated.

It is an object of the present invention to provide IOL injectors having an enhanced degree and feel of control of the plunger as it is advanced through the injector.

It is a further object of the present invention to make the enhanced control feature simple and economical to use.

It is yet another feature of the present invention to make the element that provides the additional control in a disposable form so that a fresh element can be used with each use of the injector.

BRIEF DESCRIPTION OF THE DRAWINGS

These and further objects of the present invention will become apparent upon consideration of the accompanying drawings in which.

DETAILED DESCRIPTION OF THE DRAWINGS

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

Figure 1:
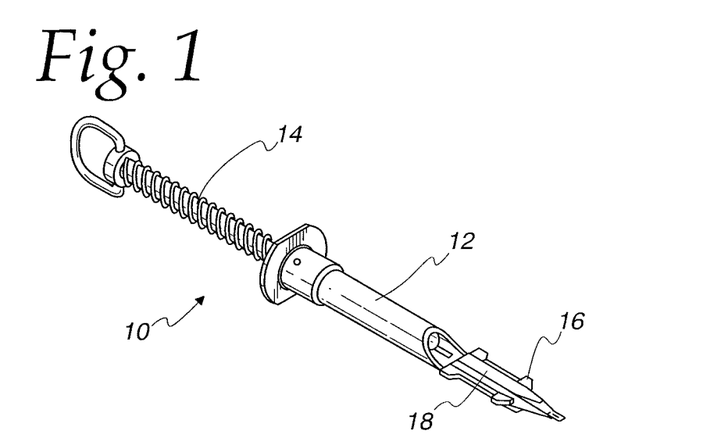
FIG. 1 is a perspective view of an IOL injector embodying certain principles of the present invention.

Referring now to FIG. 1, the numeral 10 identifies an IOL injector embodying certain aspects of the present invention. Injector 10 has an injector body 12 which slidably receives a plunger 14 at one end thereof (herein referred to as the proximal end). A cartridge holding station 16 is formed at the other end of injector body 12 (herein referred to as the distal end), which is sized and shaped to receive and hold an IOL-containing cartridge 18. Cartridge 18 has an IOL already preloaded therewithin.

Figure 2:
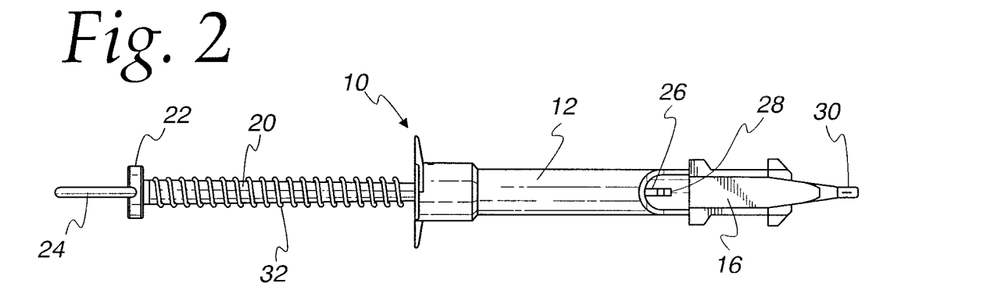
FIG. 2 is a top plan view of the injector of FIG. 1.

Referring now to FIG. 2, plunger 14 is shown as having a handle portion 20 terminating in flange 22 to which a finger grip 24 is attached. Plunger 14 also comprises a pusher portion 26 which terminates in a pusher tip 28 which, when handle 20 is advanced into body 12, enters cartridge 16 and expresses the IOL held therein through cartridge nozzle 30. A spring 32 is positioned around handle portion 20 and acts to dampen the movement of plunger 14 as will be described.

Figure 3:
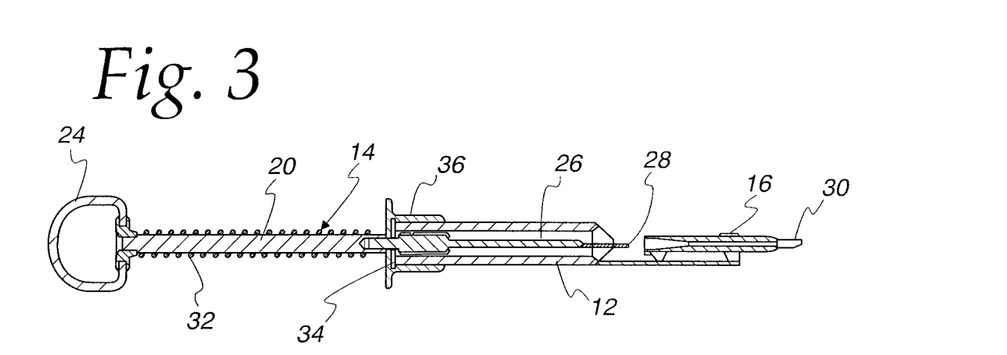
FIG. 3 is a lateral sectional view of the injector of FIG. 1.

Referring now to FIG. 3, injector 10 is shown in a lateral sectional view. Body 12 is hollow and is closed off at the proximal end 34 by cap 36. Preferably, cap 36 is removably attached to body 12 to allow plunger 14 to be removed from injector 10 so that plunger 14 and body 12 may be sterilized after use. The plunger 14 defines a central axis "A" therethrough, extending from the handle portion 20 to the pusher portion 26.

Figure 4:
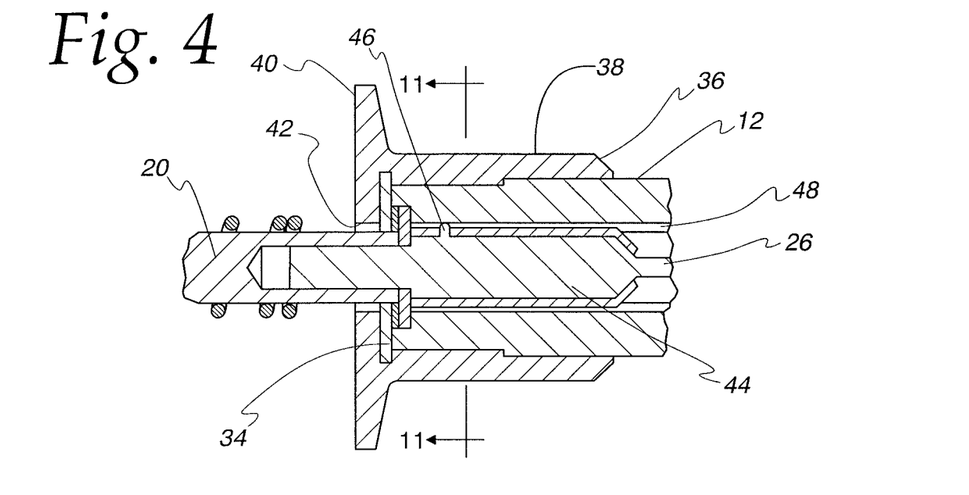
FIG. 4 is an enlarged detail of FIG. 3.

Referring now to FIG. 4, it can be seen that cap 36 has an outer cylindrical wall 38 terminating at one end in an integrally formed flange 40 which acts as a finger grip when injector 10 is being used. As seen in FIG. 4, cap 36 has a centrally-formed aperture 42 positioned on flange 40 through which handle portion 20 of plunger 14 passes and is slidably held.

Plunger 14 further comprises a barrel portion 44 formed intermediate handle portion 20 and pusher portion 26 that is radially enlarged relative to portions of the planer at the axially opposite ends of the barrel portion 44. As seen in FIG. 4, barrel portion 44 is larger in diameter than cap aperture 42 which prevents plunger 14 from being withdrawn from injector 10 so long as cap 36 is attached to body 12. Pusher portion 26 is integrally formed with barrel portion 44.

Plunger 14 is constrained to move in a straight line when it is advanced into or retracted from body 12 by a guide pin 46 which is fixedly formed on and projects radially outwardly from, the barrel portion 44 and is received by a guide groove/slot 48 formed along the interior surface of body 12 and extending only partially through a thickness of the body 12 in a radial direction. As shown, guide slot 48 extends for substantially the length of body 12 and guide pin 46 slides within and remains within guide slot 48 as plunger 14 is extended from and pushed through body 12. This keeps tip 28 properly aligned to contact an IOL held in cartridge 16 and move it toward nozzle 30. This feature is shown in further detail in FIG. 11.

Figure 5:
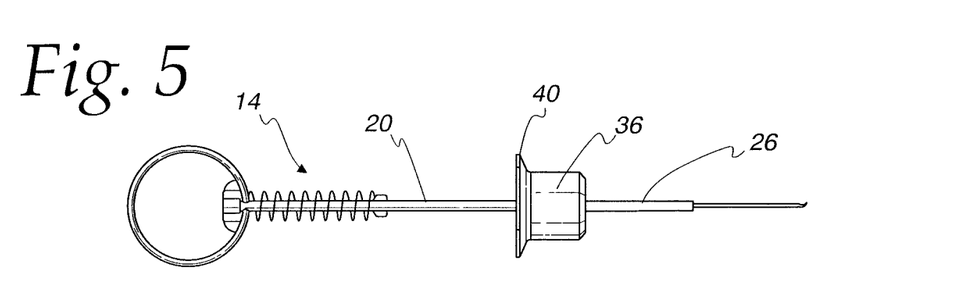
FIG. 5 a first perspective view of the injector plunger of FIG. 1.

Referring now to FIG. 5, plunger 14 and cap 36 are shown detached from body 12. As shown, handle portion 20 is pulled outward with barrel portion 44 within and concealed by cap 36. As described above, the enlarged diameter of barrel portion 44 with respect to cap aperture 42 prevents plunger assembly 14 from disengaging cap 36. Plunger assembly 14 can be disengaged from cap 36 by removing finger grip 24 and unscrewing handle flange 22.

Figure 6:
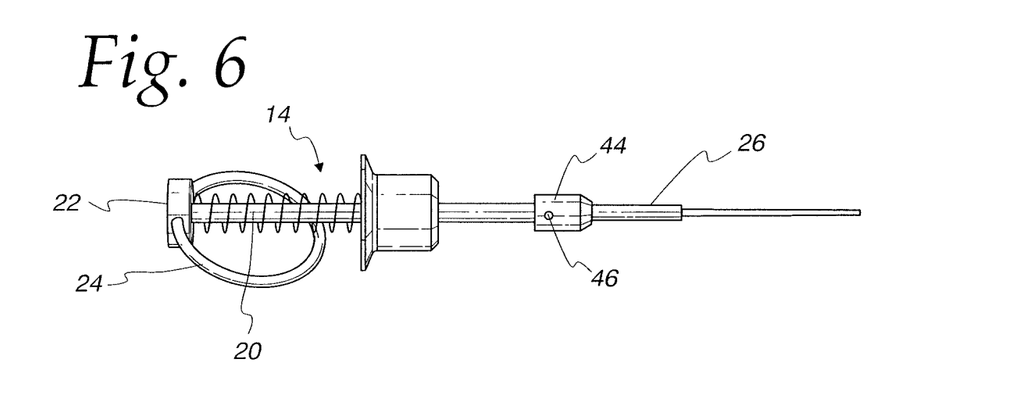
FIG. 6 is a second perspective view of the injector plunger of FIG. 1.

Referring now to FIG. 6, plunger assembly 14 is shown advanced through cap 36 with barrel portion 44 and guide pin 46 revealed.

Figure 7:
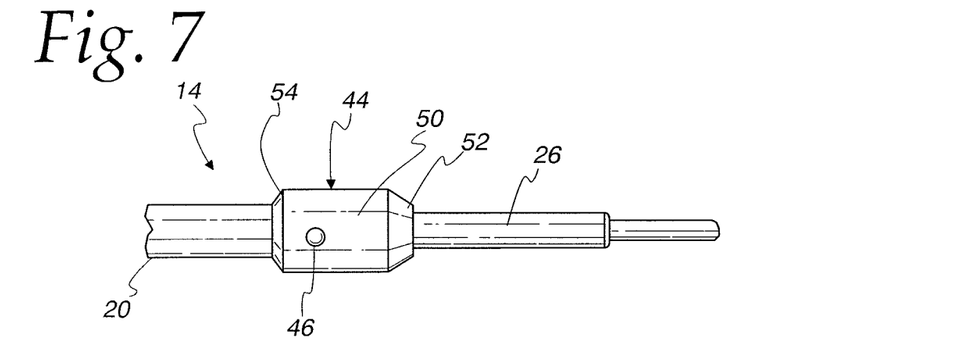
FIG. 7 is an enlarged detail of the plunger of FIG. 6.

Referring now to FIG. 7, an enlarged view of the barrel portion of plunger 14 is shown. Preferably, barrel portion 44 has a generally cylindrical body portion 50 with a uniform diameter and terminating in a first frustoconical end 52 and a second beveled end 54. In the embodiment shown, frustoconical end 52 faces the direction in which plunger 14 is advanced into injector body 12.

The body portion 50 extends axially a distance greater than the axial dimension of the tapered portion of the barrel.

Figure 8:
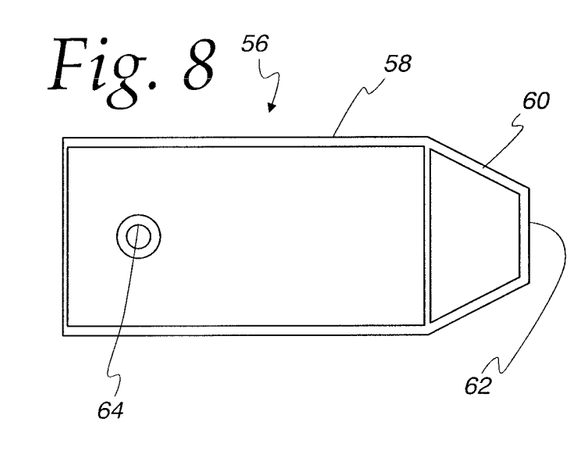
FIG. 8 is a lateral elevation view of a plunger sleeve.

Referring now to FIG. 8, a plan view of a barrel sleeve 56 is shown. Sleeve 56 is formed of an elastomeric material having controlled lubricious properties. Preferably, elastomeric materials such as silicone, rubber and the like may be used.

Figure 9:
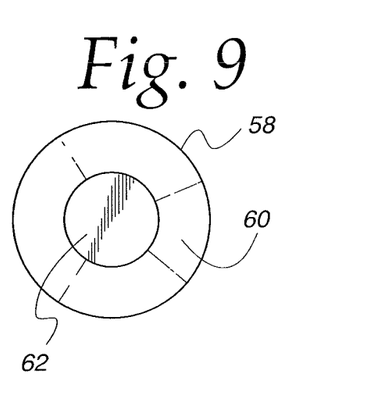
FIG. 9 is an end view of the sleeve of FIG. 8.

As seen in FIG. 8, sleeve 56 has a first body wall 58 preferably formed as a right circular cylinder. The shape of body wall 58 can be seen in FIG. 9. Preferably, the internal dimensions of body wall 58 closely match the external dimensions of barrel body portion 50.

As seen in FIG. 8, sleeve 56 terminates in a tapered, frustoconical wall 60 with leading and trailing ends and which defines a sleeve mouth 62. Preferably, the interior configuration and dimensions of sleeve body wall 60 closely match the exterior configuration and dimensions of frustoconical section 52 of barrel 44, The tapered sleeve portion has a substantially uniform thickness and extends up to distal/leading end of the tapered b el portion. As seen in FIG. 8, sleeve 56 has a pin aperture 64 formed through body wall 58.

Figure 10:
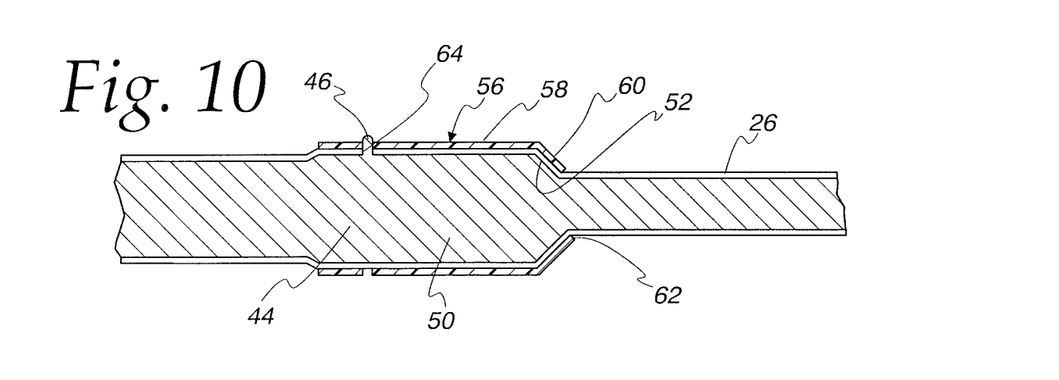
FIG. 10 is a partial lateral sectional view of the plunger shown in FIG. 5 with the sleeve applied.

Referring now to FIG. 10, sleeve 56 is shown positioned on barrel 44 of plunger assembly 14. As seen, pin aperture 64 has a surface that is sized and positioned to closely surround and engage guide pin 44, sleeve 58 closely engages the exterior surface of barrel body portion 50 and frustoconical section 60 closely engages frustoconical section 52 of barrel 44. Pusher portion 26 extends through sleeve mouth 62 as shown.

The body wall 58 extends axially a greater distance than the anal extent of tapered wall 60.

Figure 11:
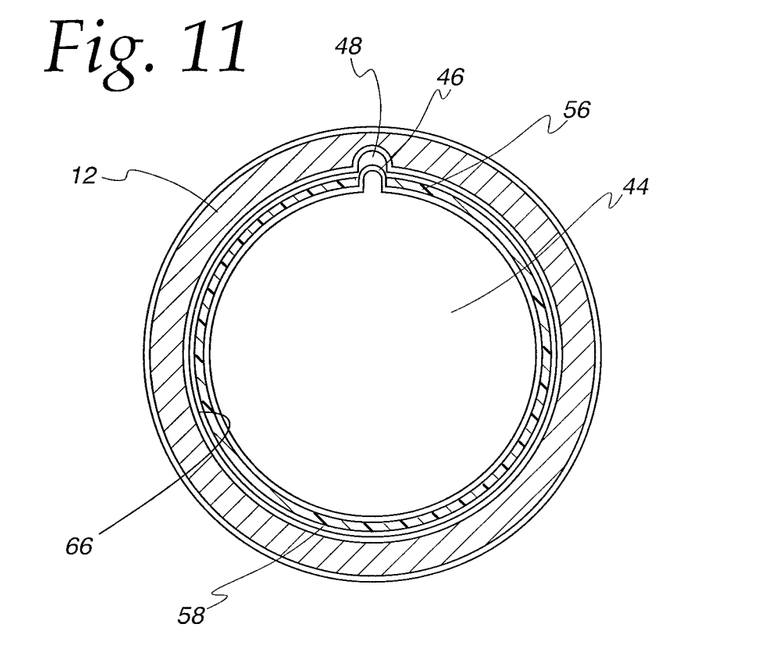
FIG. 11 is a view along 11-11 of FIG. 4.

Referring now to FIG. 11, sleeve 56 is shown positioned on barrel 44 engaging sleeve body 58 and interior wall 66 of body 12. Thus positioned, sleeve 56 provides resistance to the movement of plunger 14 through body 12. The amount and character of this resistance can be altered by selecting various materials and thicknesses for sleeve 56. Sleeve 56 remains in contact with interior wall 66 throughout the forward motion of plunger assembly 14 through body 12 and is held in the same operative position on the barrel body by the engagement of body wall 58 with barrel body portion 50, by the engagement of frustoconical wall 60 with frustoconical portion 52 and by the engagement of guide pin 44 with aperture 64 as the plunger assembly moves in a range between fully extended and retracted positions. The guide pin 44 and frustoconical portion 52 define spaced, axially oppositely facing surfaces that block the sleeve 56 to thereby maintain the sleeve 56 in the same axial position on the barrel portion. The pin 46 blocks both rotational and sliding movement of the sleeve 56 relative to the barrel body portion 50.

After the injector has been used to express the IOL from cartridge 16, plunger 14 is disengaged from body 12 and the used sleeve 56 is removed and discarded. Thereafter, plunger 14, cap 36 and body 12 are sterilized for re-use. After sterilization and prior to surgery, a medical assistant will apply a new sleeve 56 to plunger 14, observing good sterile technique, and then assemble plunger 14 to body 12 so that injector 10 is ready for use during the next surgery.

Preferably, cap 36 is mounted to body 12 without requiring the use of fasteners, making it easy to disassemble and reassemble injector 10.

The present embodiment has shown the use of sleeve 56 with a damping spring 32. It is contemplated that such an arrangement can be used. It is also contemplated that other damping devices may be combined with the use of sleeve 56 with the goal being to produce an injector 10 that has a comfortable and reproducible feel to a surgeon and will allow the surgeon to accurately express an IOL from a cartridge successfully.

It is further contemplated that selecting a desired material for sleeve 56 and a desired stiffness for spring 32 will provide a number of different handling characteristics for injector 10.

It is also contemplated that the appropriate selection of a material and size for sleeve 56 will enable injector 10 to be used without a damping spring 32.

What is claimed is:

1. An intraocular lens injector device configured to inject an intraocular lens, the intraocular lens injector device comprising:
   a hollow injector body having a distal end, a proximal end, and an interior surface defining a central passage through the injector body;
   a plunger sized and shaped to fit into the injector body central passage and defining a central axis therethrough, the plunger having a proximal handle portion for being engaged by a user and an operative distal tip portion, the plunger having a barrel portion with proximal/trailing and distal/leading ends and formed intermediate the handle portion and the tip portion, the barrel portion sized and shaped to move along at least a portion of the central passage, the barrel portion having an exterior surface, the plunger having a range of movement relative to the injector body between fully extended and retracted positions,
   wherein the barrel portion is radially enlarged relative to portions of the plunger at the leading and trailing ends of the barrel portion; and
   a sleeve made from an elastomeric material and sized and shaped to fit around the barrel portion, the sleeve having a sleeve interior surface for contacting the barrel portion exterior surface, the sleeve having an exterior surface for contacting the injector body interior surface for damping movement of the plunger through the central passage, the sleeve having a sleeve thickness between the sleeve interior and exterior surfaces in a direction radial to the central axis, the sleeve being movable with the plunger with respect to the injector body,
   the injector configured so that the sleeve is blocked by spaced, axially oppositely facing surfaces on the plunger so as to thereby be maintained in a same axial position on the barrel portion as the plunger moves between the fully extended and retracted positions,
   wherein the sleeve has an axial dimension that is greater than the thickness of the sleeve,
   wherein the barrel portion has a guide pin fixedly formed thereon and projecting radially outwardly from the barrel portion,
   wherein the guide pin defines one of the axially oppositely facing surfaces on the plunger.

2. The intraocular lens injector device as recited in claim 1 wherein a portion of the injector body interior surface has a guide groove, and the guide pin is sized and shaped to fit within and travel along the guide groove.

3. The intraocular lens injector device as recited in claim 2 wherein the sleeve has a pin aperture formed through the sleeve interior and exterior surfaces, and the pin aperture sized and positioned to fit over the guide pin when the sleeve is placed on the barrel portion, wherein the pin aperture has a surface that directly surrounds the guide pin.

4. The intraocular lens injector device as recited in claim 3 wherein the barrel portion has a tapered portion at the leading end of the barrel portion, and the sleeve has a tapered portion sized to fit over the tapered barrel portion, wherein the tapered barrel portion has leading and trailing ends and defines the other of the axially oppositely facing surfaces on the plunger, wherein the sleeve extends up to the distal/leading end of the tapered barrel portion.

5. The intraocular lens injector device as recited in claim 4 wherein the barrel portion has a uniform diameter portion extending from the trailing end of the tapered barrel portion to the proximal end of the barrel portion and the barrel portion with the uniform diameter has an axial extent greater than an axial extent of the tapered barrel portion.

6. The intraocular lens injector device as recited in claim 3 wherein the pin blocks relative movement between the sleeve and barrel portion around the central axis.

7. The intraocular lens injector device as recited in claim 3 wherein the pin blocks relative movement between the sleeve and barrel portion along the central axis to thereby cause the sleeve to follow movement of the barrel portion in an axial direction.

8. The intraocular lens injector device as recited in claim 2 wherein the guide groove extends only partially through a thickness of the injector body in a radial direction.

9. The intraocular lens injector device as recited in claim 1 wherein the sleeve is formed from rubber.

10. The intraocular lens injector device as recited in claim 1 wherein the sleeve is formed from silicone.

11. The intraocular lens injector device as recited in claim 1 further comprising a damping spring.

12. The intraocular lens injector device as recited in claim 1 wherein the sleeve extends up to the distal/leading end of the tapered barrel portion.

13. An intraocular lens injector device configured to inject an intraocular lens, the intraocular lens injector device comprising:
    a rigid, hollow injector body having a distal end, a proximal end, and an interior surface defining a central passage through the injector body;
    a rigid plunger sized and shaped to fit into the injector body central passage and defining a central axis therethrough, the plunger having a proximal handle portion for being engaged by a user and an operative distal tip portion, the plunger having a barrel portion formed intermediate the handle portion and the tip portion, the barrel portion having a cylindrically shaped portion with a radially outwardly facing surface and a leading tapered surface with axially spaced leading and trailing ends and, the barrel portion sized and shaped to move along at least a portion of the central passage, the plunger having a range of movement relative to the injector body between fully extended and retracted positions; and
    a flexible, elastomeric sleeve sized and shaped to fit around the barrel portion, the sleeve having a sleeve interior surface for contacting the radially outwardly facing surface of the cylindrically shaped portion and the leading tapered barrel surface, the sleeve having an exterior surface for contacting the injector body interior surface for damping movement of the plunger through the central passage, the injector configured so that the sleeve is maintained in a same axial position on the barrel portion as the plunger moves between the fully extended and retracted positions, the sleeve having a sleeve thickness between the sleeve interior and exterior surfaces in a direction radial to the central axis, wherein the sleeve has an axial dimension that is substantially greater than the thickness of the sleeve, wherein the sleeve terminates at the leading axial end of the leading tapered barrel surface, wherein the sleeve has a cylindrical wall extending into a leading tapered wall with the leading tapered wall sized to fit over the leading tapered barrel surface, wherein the sleeve exterior surface has a shape that conforms substantially to a shape of the leading tapered barrel surface and a wall of the sleeve has a uniform thickness where the sleeve extends along the leading tapered barrel surface, wherein the leading tapered wall of the sleeve has a uniform thickness where the sleeve extends along the leading tapered barrel surface and the cylindrical wall of the sleeve has a uniform thickness over an axial extent of the cylindrically shaped portion of the barrel portion.

14. The intraocular lens injector device as recited in claim 13 wherein the sleeve interior surface has a shape that conforms substantially to the shape of the leading tapered barrel surface.

15. The intraocular lens injector device as recited in claim 13 wherein the barrel portion is radially enlarged relative to portions of the plunger at leading and trailing ends of the barrel portion.

16. An intraocular lens injector device configured to inject an intraocular lens, the intraocular lens injector device comprising:

a hollow injector body having a distal end, a proximal end, and an interior surface defining a central passage through the injector body;

a plunger sized and shaped to fit into the injector body central passage and defining a central axis therethrough, the plunger having a proximal handle portion for being engaged by a user and an operative distal tip portion, the plunger having a barrel portion with proximal/trailing and distal/leading ends and formed intermediate the handle portion and the tip portion, the barrel portion sized and shaped to move along at least a portion of the central passage, the barrel portion having an exterior surface, the plunger having a range of movement relative to the injector body between fully extended and retracted positions; and a sleeve made from an elastomeric material and sized and shaped to fit around the barrel portion, the sleeve having a sleeve interior surface for contacting the barrel portion exterior surface, the sleeve having an exterior surface for contacting the injector body interior surface for damping movement of the plunger through the central passage, the sleeve having a sleeve thickness between the sleeve interior and exterior surfaces in a direction radial to the central axis, the sleeve being movable with the plunger with respect to the injector body, the injector configured so that the sleeve is blocked by spaced, axially oppositely facing surfaces on the plunger so as to thereby be maintained in a same axial position on the barrel portion as the plunger moves between the fully extended and retracted positions, wherein the sleeve has an axial dimension that is substantially greater than the thickness of the sleeve, wherein the barrel portion has a guide pin fixedly formed thereon and projecting radially outwardly from the barrel portion, wherein the guide pin defines one of the axially oppositely facing surfaces on the plunger, wherein a portion of the injector body interior surface has a guide groove, and the guide pin is sized and shaped to fit within and travel along the guide groove, wherein the guide groove extends only partially through a thickness of the injector body in a radial direction.

17. An intraocular lens injector device configured to inject an intraocular lens, the intraocular lens injector device comprising:

a hollow injector body having a distal end, a proximal end, and an interior surface defining a central passage through said injector body;

a plunger sized and shaped to fit into the injector body central passage and defining a central axis therethrough, the plunger having a proximal handle portion for being engaged by a user and an operative distal tip portion, the plunger having a barrel portion with proximal/trailing and distal/leading ends and formed intermediate the handle portion and the tip portion, the barrel portion sized and shaped to move along at least a portion of the central passage, the barrel portion having an exterior surface, the plunger having a range of movement relative to the injector body between fully extended and retracted positions; and a sleeve made from an elastomeric material and sized and shaped to fit around the barrel portion, the sleeve having a sleeve interior surface for contacting the barrel portion exterior surface, the sleeve having an exterior surface for contacting the injector body interior surface for damping movement of the plunger through the central passage, the sleeve having a sleeve thickness between the sleeve interior and exterior surfaces in a direction radial to the central axis, the sleeve being movable with the plunger with respect to the injector body, the injector configured so that the sleeve is blocked by spaced, axially oppositely facing surfaces on the plunger so as to thereby be maintained in a same axial position on the barrel portion as the plunger moves between the fully extended and retracted positions, wherein the sleeve has an axial dimension that is substantially greater than the thickness of the sleeve, wherein the barrel portion has a guide pin fixedly formed thereon and projecting radially outwardly from the barrel portion, wherein the guide pin defines one of the axially oppositely facing surfaces on the plunger, wherein a portion of the injector body interior surface has a guide groove, and the guide pin is sized and shaped to fit within and travel along the guide groove, wherein the sleeve has a pin aperture formed through the sleeve interior and exterior surfaces, and the pin aperture sized and positioned to fit over the guide pin when the sleeve is placed on the barrel portion, wherein the pin aperture has a surface that surrounds the guide pin, wherein the barrel portion has a tapered portion at the leading end of the barrel portion, and the sleeve has a tapered portion sized to fit over the tapered barrel portion, wherein the tapered barrel portion has leading and trailing ends and defines the other of the axially oppositely facing surfaces on the plunger, wherein the barrel portion has a uniform diameter portion extending from the trailing end of the tapered barrel portion to the proximal end of the barrel portion and the barrel portion with the uniform diameter has an axial extent greater than an axial extent of the tapered barrel portion.

18. An intraocular lens injector device configured to inject an intraocular lens, the intraocular lens injector device comprising:

a hollow injector body having a distal end, a proximal end, and an interior surface defining a central passage through said injector body;

a plunger sized and shaped to fit into the injector body central passage and defining a central axis therethrough, the plunger having a proximal handle portion for being engaged by a user and an operative distal tip portion, the plunger having a barrel portion with proximal/trailing and distal/leading ends and formed intermediate the handle portion and the tip portion, the barrel portion sized and shaped to move along at least a portion of the central passage, the barrel portion having an exterior surface, the plunger having a range of movement relative to the injector body between fully extended and retracted positions; and a sleeve made from an elastomeric material and sized and shaped to fit around the barrel portion, the sleeve having a sleeve interior surface for contacting the barrel portion exterior surface, the sleeve having an exterior surface for contacting the injector body interior surface for damping movement of the plunger through the central passage, the sleeve having a sleeve thickness between the sleeve interior and exterior surfaces in a direction radial to the central axis, the sleeve being movable with the plunger with respect to the injector body, the injector configured so that the sleeve is blocked by spaced, axially oppositely facing surfaces on the plunger so as to thereby be maintained in a same axial position on the barrel portion as the plunger moves between the fully extended and retracted positions, wherein the sleeve has an axial dimension that is substantially greater than the thickness of the sleeve, wherein the barrel portion has a guide pin fixedly formed thereon and projecting radially outwardly from the barrel portion, wherein the guide pin defines one of the axially oppositely facing surfaces on the plunger, the barrel portion having a tapered distal/leading end, wherein the sleeve extends up to the distal/leading end of the tapered barrel portion.

* * * * *